United States Patent [19]

Braden William I.

[11] Patent Number: 4,673,650

[45] Date of Patent: Jun. 16, 1987

[54] PROTEIN HARVESTING SYSTEM

[75] Inventor: Braden William I., Norfolk, Mass.

[73] Assignee: Damon Biotech, Inc., Needham Heights, Mass.

[21] Appl. No.: 845,503

[22] Filed: Mar. 28, 1986

[51] Int. Cl.$^4$ .................................................. C12M 3/02
[52] U.S. Cl. ...................................... 435/286; 435/284; 435/288; 435/316; 264/4.3
[58] Field of Search ............... 435/284, 286, 288, 316, 435/287; 264/4.3; 427/213.31

[56] References Cited

U.S. PATENT DOCUMENTS

| | | |
|---|---|---|
| 4,251,387 | 2/1981 | Lim et al. ............................ 252/316 |
| 4,352,883 | 10/1982 | Lim ..................................... 435/178 |
| 4,407,957 | 10/1983 | Lim ..................................... 435/178 |
| 4,409,331 | 10/1983 | Lim ..................................... 435/178 |

Primary Examiner—Samuel Scott
Assistant Examiner—Allen J. Flanigan
Attorney, Agent, or Firm—Lahive & Cockfield

[57] ABSTRACT

Disclosed is a large scale apparatus for the harvesting cell products secreted from cells grown within semipermeable artificial membranes. The apparatus comprises a number of cooperating processing stations which perform the various steps necessary in the harvesting of cell product. Included within the apparatus is a holding tank for receiving mature encapsulated cells and cell medium, as well as any reagents, from separate storage sources, used in the process. Also included, and in fluid communication with the holding tank, is a shearing station where the capsule membranes are ruptured to free the encapsulated cell product, and a separating station where the liquid cell product is separated from solid components such as cell membrane debris and cells. The apparatus may include a microprocessor which generates control signals to enhance the level of automation of the apparatus.

17 Claims, 3 Drawing Figures

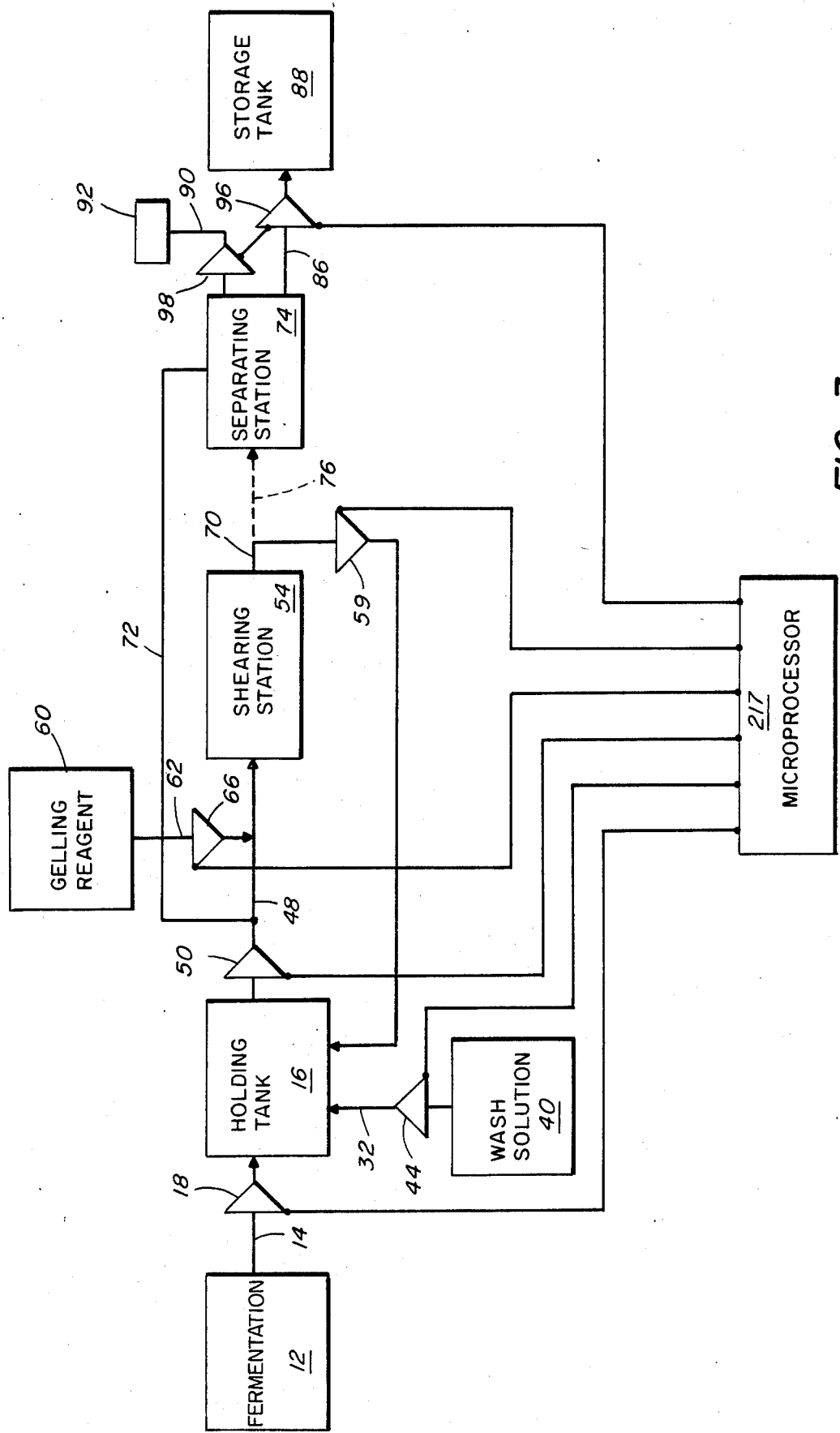

PROTEIN HARVESTING SYSTEM

BACKGROUND OF THE INVENTION

This invention relates to the recovery of substances secreted by cells. More particularly, this invention relates to the recovery of cell products produced by encapsulated cells.

It is known that cells may be grown within capsules having semipermeable membranes. The encapsulated cells are dispersed in a cell growth medium which includes all components necessary for cell metabolism and ongoing viability. The encapsulated cells may be modified cells, such as hybridomas or myelomas, adapted to produce large quantities of cell products such as proteins or other substances of interest. Typically, the capsule membranes are permeable to molecules having a lower molecular weight such as ions, amino acids, cell wastes and cell nutrients suspended in the growth medium. The membranes generally are constructed so as to be impermeable to higher molecular weight materials, particularly products secreted by the cells. Techniques for cell encapsulation are disclosed in U.S. Pat. Nos. 4,409,331 to Lim; 4,251,387 to Lim et al; and 4,352,883 to Lim, each of which is hereby incorporated by reference. It is possible to regulate the permeability of the capsule membrane as disclosed in the above-referenced patents and as disclosed in copending U.S. application Ser. No. 579,494 which is also hereby incorporated by reference.

The membranes typically used to encapsulate viable cells are generally constructed of a first, gellable layer of a polysaccharide material such as an alkalai metal alginate. This first layer is permanently cross linked upon contact with a polymer having plural reactive groups such as polylysine. A more detailed description of the capsule membranes and their formation techniques is provided in the above-referenced patents, particularly U.S. Pat. No. 4,352,883.

Of particular interest in the field of biotechnology is the genetic modification of cells to yield cells capable of secreting relatively large quantities of a product of interest such as proteins or other biological agents having important medical, pharmaceutical, or industrial applications. Current noteworthy products of modified cells include monoclonal antibodies. Although biological agents such as monoclonal antibodies may be sufficiently and conveniently produced by cells and collected within membranes which enclose the cells, as described above, the recovery of the cell product from within the encapsulating membrane can be quite tedious.

Recovery of the cell product from within the volume defined by the capsule membranes typically involves a number of tedious manual steps during which there exists the possibility that the cell product will be contaminated, or that all or part of the product will be lost or damaged to the extent that it is not usable. One important step of the typical recovery process is to rupture the capsule membrane to release the encapsulated cell product. Eventually the cell product must be isolated from the capsule membrane debris and the cells. Other steps such as washing and purification are also involved in this process. As a result of the numerous manual steps involved in this process, the recovery of a relatively pure cell product from within capsules membranes is quite time consuming and economically inefficient.

Accordingly, there is a need for a system or apparatus which automatically and/or sequentially performs the steps necessary to recover the cell product from the encapsulated environment with little or no human intervention. A useful apparatus would decrease the time necessary to recover cell products and would reduce the chance of contamination or loss of the product, thereby making the production and collection of cell products more economically feasible.

SUMMARY OF THE INVENTION

An object of this invention is to provide an apparatus for rapidly and conveniently recovering cell products from within capsules containing the producing cells, the cell product and other materials. Another object of this invention is to provide such an apparatus which produces a relatively complete yield of a relatively pure cell product. It is a further object of this invention to provide such an apparatus which maintains the sterility of the cell product throughout the separation process.

The invention provides an apparatus for the recovery of useful cell products which are produced by cells encapsulated within semipermeable membranes. The membranes possess a level of permeability such that higher molecular weight materials such as the cell product and cells are retained within the membrane. Other materials of a lower molecular weight are able to traverse the capsule membrane. The apparatus recovers a relatively pure cell product which is substantially free of capsule membrane components, cells and other biological materials present within the capsule volume.

The types of cell products which may be recovered by the apparatus of this invention are virtually unlimited, and depend only on the specific cell line being cultured. Examples of such cell products include monoclonal antibodies, interferons, plasminogen activators, and hormones.

The present apparatus comprises a number of interrelated stations, each of which perform a certain step of the overall process necessary to recover the extracellular, intracapsular cell product. A sterile holding tank is provided for receiving mature, encapsulated cells and growth medium. The holding tank has an intake port in fluid communication with fermentation tanks where the cells are grown. The holding tank may also be equipped with one additional intake port for introducing useful reagents and other materials to the holding tank. At least one output port is provided on, or adjacent to, the bottom surface of the tank for draining cells and liquids, including waste. A port for discharging waste fluids is equipped with an element which, when necessary, precludes the passage of capsules from the tank while permitting the passage of fluids.

In a preferred embodiment the holding tank has a stirring means such as a motor-driven paddle as well as pressure and temperature control means.

The apparatus also includes a source of wash solution which is in fluid communication with an input port of the sterilizable holding tank. The wash solution is selectively transportable to the holding tank by means of valves and a pump which control the flow of solution from its source to the holding tank.

Provided downstream of and in communication with the holding tank is a shearing station. The shearing station includes an input port for receiving encapsulated cells and solution from the holding tank, and an output port. The shearing station also includes motor-driven shearing means to disrupt the capsule membranes while leaving the cell membranes intact, thus producing a homogenate comprising a solid phase of capsule debris and cells, and a liquid phase comprising the dissolved cell product and the gellable material.

A selectively operable source of a gelling reagent is disposed upstream of and in fluid communication with the shearing station. The manipulation of valves and a pump enables the gelling solution to flow from its source into the shearing station where it reacts with the gellable material, causing it to precipitate for removal from solution.

The present apparatus also includes a separating station which is disposed downstream of and in direct or indirect fluid communication with the shearing station. The separating station is equipped with an input port in communication with the upstream station. The separating station comprises a centrifuge, or similar separation device, which separates the liquid cell product fraction from the solid fraction. First and second output ports are provided for removing liquid and solid fractions, respectively, from the separating station. Preferably, the first output port is in fluid communication with a sterile storage tank which receives the cell product and maintains it under optimal environmental conditions. The second output port may be in communication with a waste receptacle to facilitate disposal of the solid waste fraction.

In a preferred embodiment, valves and pumps, where necessary, are provided to facilitate efficient fluid flow. The cell product recovery apparatus may also include a microprocessor which is programmed to provide control signals to the various elements of the apparatus such as valves, pumps and processing stations, in a predetermined, timed sequence, to enhance the level of automation of the system.

BRIEF DESCRIPTION OF THE DRAWINGS

For a fuller understanding of the nature and objects of the invention, reference should be made to the following detailed description and the accompanying drawings in which:

FIG. 3 is a block diagram illustrating an alternative embodiment of the apparatus and process of FIGS. 1 and 2.

Like reference characters in the respective drawn figures indicate corresponding parts.

DESCRIPTION

Figure 1:
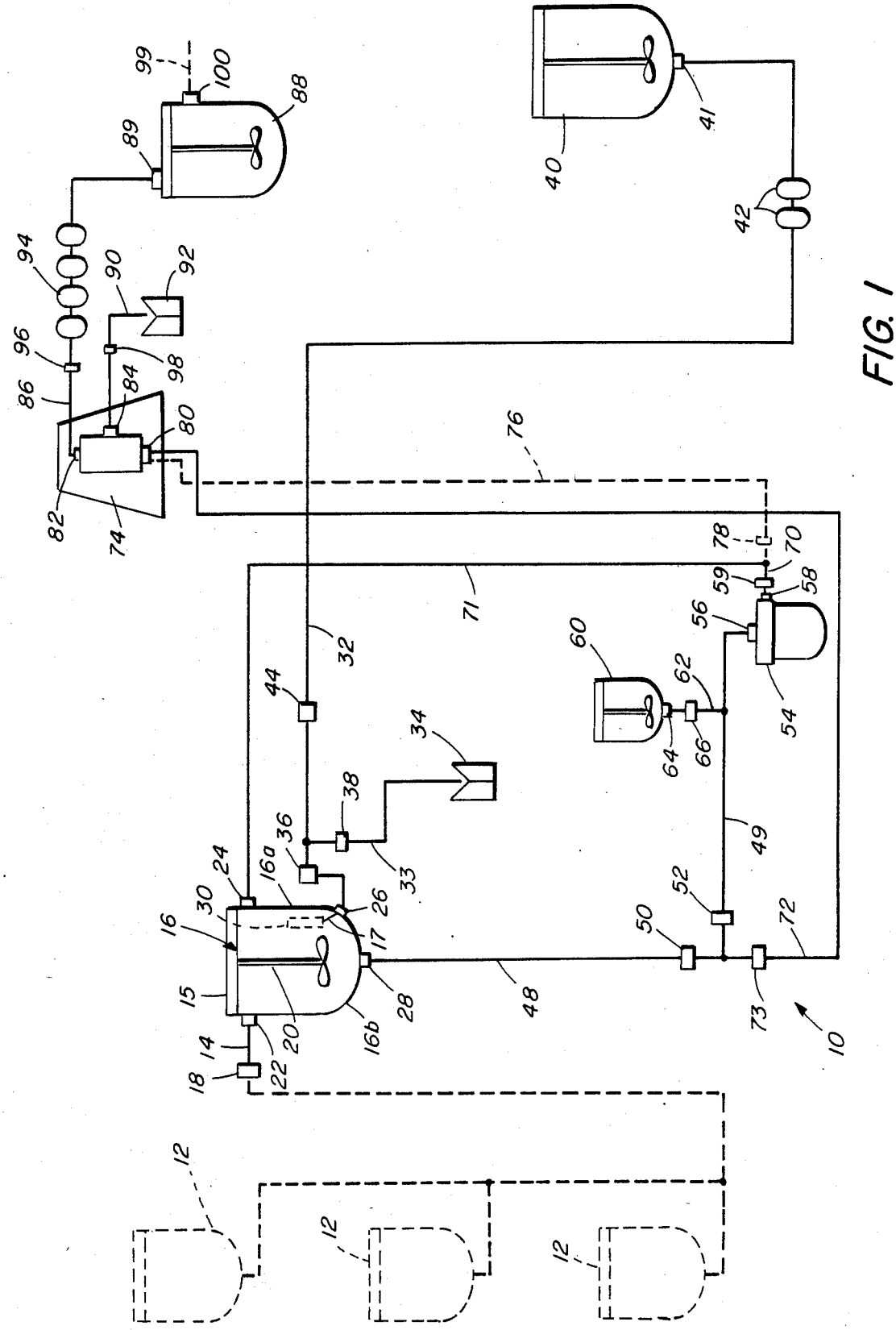
FIG. 1 is a schematic diagram illustrating one embodiment of the apparatus of the invention.
Figure 2:
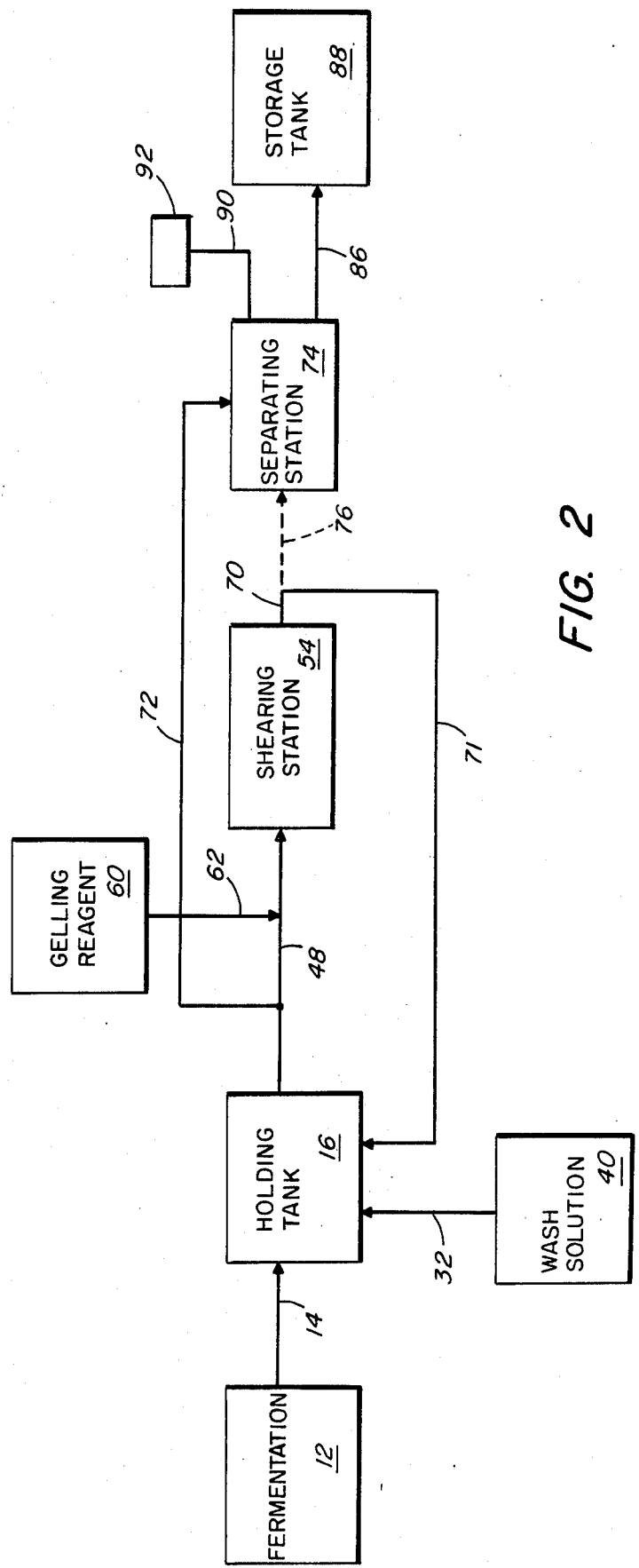
FIG. 2 is a block diagram illustrating the process of the embodiment of the apparatus shown in FIG. 1.

Referring to FIGS. 1 and 2, the apparatus 10 of this invention comprises a number of interrelated stations which cooperate to extract cell product (usually a protein) produced by cells grown within capsules having semipermeable membranes. The stations of the apparatus separate the water soluble cell product from extracapsular materials, cells and the myriad proteins they contain, and capsule membrane components.

As illustrated in the embodiments of FIGS. 1 and 2, the encapsulated cells are disposed within a cell culture medium and grown within sterile fermentation tanks 12 (not necessarily a part of the present apparatus). The encapsulated cells typically comprise approximately 20% of the initial volume of the medium-capsule suspension, and range in size from approximately 100 microns to 2 millimeters, but are preferably 400 to 600 microns. Of course, the environment within which the cells are grown will vary with the requirements of the particular cell line being developed, and may be regulated by the apparatus to maintain cell viability and to promote mitosis.

FIG. 1 depicts a currently preferred embodiment of the cell product extracting apparatus of this invention. The apparatus comprises a sterile holding tank 16, a source of wash solution 40, a shearing station 54, a source of gelling solution 60, a separating station 74, a sterile storage tank 88, and the fluid pathways, valves and pumps which facilitate fluid communication between the various elements and stations of the apparatus.

Holding tank 16 comprises a stainless steel vessel having side and bottom walls 16a, 16b and a capacity of approximately 1000 liters. A removable top cover 15 is adapted for securely mating to the tank 16. Cover 15 preferably includes a sterilizable elastomeric seal (not shown). As illustrated in FIG. 1, tank 16 also comprises input ports 22, 24 disposed opposite each other along the upper portion of side walls 16a. The tank also features an output port 28 disposed along the bottom wall 16b and an input-output port 26 disposed along the bottom wall adjacent port 28. Port 26 is equipped with a filter element 30, vertically disposed within tank 16, which precludes the passage of capsules from the tank while allowing fluid to pass from the tank. Filter element 30 comprises two adjacent screen filters, each having a mesh size of approximately 300 microns. The filters are joined together on all sides and are spaced apart by a void of approximately 1 inch. Filter element 30 communicates with port 26 through conduit 17 which is connected between port 26 and a bottom wall of the filter element. Waste fluid is allowed to flow through filter 30 into conduit 17 and through port 26. Capsules, which are typically too large to traverse the screens, remain outside filter element 30 and are retained within tank 16. Additional fluids added through port 26 pass through conduit 17 before entering tank 16. Port 28 may be opened when it is desirable to withdraw both capsules and fluid from tank 16.

It is understood that the holding tank of this invention is equally useful if equipped with other convenient arrangements of input and output ports.

Preferably, tank 16 also comprises a motor-driven paddle 20, or similar apparatus for stirring or agitating the contents of the tank. The agitation apparatus should have sufficient power to gently disperse a 1000 liter suspension having a viscosity of approximately 100 centipoise. Also, it is desirable to equip tank 16 with conventional pressure and temperature control means to provide an optimal environment for cell product yields.

A vessel 40 which serves as a source of a washing solution such as phoshate buffered saline (PBS) is disposed in fluid communication with holding tank 16. A conduit 32 provides a flow path between an output port 41 of the solution source vessel 40 and input/output port 26 of tank 16. The conduit 32 includes valves 36 and 44 for regulating the flow within the conduit, and a pump, (not shown), if necessary, to provide the motive force for fluid flow. In a preferred embodiment, conduit 32 also includes a filtering apparatus 42, to remove debris and impurities from the washing solution. The filtering apparatus 42 comprises twin, serial filters, such as a combination of depth and screen filters, having decreasing mesh sizes, in the direction of flow, of approximately 0.6 microns and 0.2 microns. Conduit 32 also communicates with a waste receptacle 34 by way of conduit 33 to facilitate the disposal of waste fluids from tank 16. Valve 38 controls the flow of liquid waste through conduit 33 to waste receptacle 34.

Disposed downstream of holding tank 16 is shearing station 54 which comprises an input port 56 and an output port 58. The shearing station 54 is preferably equipped with a continuous homogenizer such as a Ross Homogenizer, model no. 301, manufactured by Charles Ross & Son Co., 710 Old Illets Path, Hauppauge, N.Y. A homogenizer or shearing means useful with the present invention preferably utilizes a centrifugal pump, and should have a motor of approximately 1½ h.p. to enable it to process the suspension at the rate of approximately 200 liters per minute. The magnitude of the shearing force will vary with the volume and viscosity of material being processed. However, the shearing force should be sufficient to ensure relatively complete rupture of the capsule membranes, but not so great as to rupture the cell membranes.

Conduits 48 and 49 provide a flow path between input port 56 of the shearing station 54 and output port 28 of holding tank 16. Valves 50 and 52 are provided within conduits 48 and 49, respectively, to regulate the flow of fluid within the conduits.

A reservoir 60 for storing a gelling solution, such as a calcium chloride solution, is disposed upstream of shearing station 54. Reservoir 60 includes an output port 64 and a conduit 62 which provide a flow path for the gelling solution to conduit 49. Valve 66, disposed in conduit 62, regulates the flow of liquid within conduit 62.

In a preferred embodiment, conduits 70 and 71 form part of a recirculation loop and provide a fluid flow path between shearing station output port 58 and input port 24 of holding tank 16. Valve 59 regulates fluid flow within conduits 70 and 71. The recirculation loop is completed by conduits 48 and 72 which provide fluid communication means between tank 16 and an input port 80 of a downstream separating station 74. Valve 73 regulates fluid flow within conduit 72.

Separating station 74 includes an input port 80 and output ports 82 and 84. This station is equipped with a continuous centrifuge or similar device for separating the liquid phase from a solid phase. An example of a centrifuge which is suitable for use with this apparatus is a Sharples model no. AS26 centrifuge manufactured by Pennwalt, Sharples-Stokes Division, 955 Mearns Road, Warminister, Pa. Ideally, a centrifuge useful with this apparatus has a holding capacity of approximately 20 liters and operates at a speed of about 15,000 rpm.

In an alternate embodiment, the recirculation loop is replaced by conduit 76 which provides a direct flow path between conduit 70, output port 58 of shearing station 54, and the input port 80 of separating station 74. Valve 78 regulates fluid flow within conduit 76.

Storage tank 88 comprises a stainless steel vessel having an input port 89. Conduit 86 provides a flow path for recovered liquid cell product between separating station output port 82 and input port 89 of tank 88. Valve 96 regulates fluid flow within conduit 86. Preferably, conduit 86 includes serial filtering apparatus 94 having approximately four filtering elements of decreasing mesh size in the direction of flow. The mesh sizes range from a maximum size of 0.6 microns to a minimum size of 0.1 microns. Typically, the four filters will have mesh sizes of approximately 0.6, 0.45, 0.2 and 0.1 microns, respectively. Filters useful in this apparatus include screen and depth filters and combinations thereof.

Tank 88 may also be equipped with an output port 100 and conduit 99 for transporting the recovered liquid to additional processing stations.

In a preferred embodiment conduit 90 communicates with output port 84 of separating means 74, and includes valve 98. Conduit 90 provides a flow path for transporting solid waste from the separating station to a waste receptacle 92.

Preferably, the conduits of this apparatus are constructed of stainless steel or teflon and range in diameter from approximately 1 to 2 inches.

FIG. 2 illustrates the operation of the invention. The holding tank 16 is charged with mature encapsulated cells and growth medium from a fermentation area 12. A wash solution, such as PBS, is held in a storage area 40. After draining all but a small amount of growth medium from tank 16, the encapsulated cells, which remain in tank 16, are washed with approximately four volumes of PBS per liter of capsules. Each wash requires approximately 30 minutes, and the washing procedure is repeated 3-4 times. The PBS suspends the capsules and acts as a dialysate to induce smaller, extracellular, intracapsular materials having a lower molecular weight to traverse the capsule membrane into the PBS wash solution.

Following the final wash, all but a small amount of the PBS is drained from tank 16. The remaining contents of tank 16 are transported through conduit 48 to a shearing station 54. The shearing station 54 homogenizes the capsule-PBS suspension by rupturing the capsule membranes and produces a homogenate comprising cells, released cell product, and capsule membrane debris, including a gellable material such as an alginate.

When the homogenization procedure is complete a gelling solution, such as a 20% calcium chloride solution, is added to the homogenate from reservoir 60 located upstream of shearing station 54. As the gelling solution contacts and is mixed with the homogenate, it initiates precipitation of the gellable material, thereby removing the gellable material from the solution. Following the gelling reaction, the mixture exits shearing station 54 and enters a recirculation loop formed by conduits 70 and 71, which lead to holding tank 16, and conduits 48 and 72 which transport the material to downstream stations.

Conduit 72 leads to a separating station 74 where the solid and liquid components of the mixture are separated by a process such as centrifugation. The recovered liquid cell product is then transported to a holding tank 88 where it awaits further processing. The solid component is transported to a waste receptacle 92 as illustrated in FIG. 1.

In another embodiment the recirculation loop is replaced by conduit 76 which provides a direct flow path to separating station 74 from shearing station 54 and conduit 70.

The conduit configurations illustrated in the drawings and described above are intended to be exemplary. It is to be understood that a great many conduit configurations could be used effectively with this apparatus. It is also understood that the placement of valves within the conduits may vary from that illustrated and described herein.

Although not illustrated in the drawings, it is understood that the flow paths of this apparatus should be equipped with pumps, or similar devices, to provide for the active transport of fluids through the conduits. The type and placement of the pumps is largely a matter of design choice and is well within the skill of the art. A recommended pump is a Waukesha Positive Displacement 10 horsepower pump having the ability to create fluid flow rates ranging from 10 to 100 liters per minute.

The present invention may also be adapted to operate with enhanced automation, as illustrated in FIG. 3, whereby each processing station and the timing of each processing step of this apparatus is controlled by a microprocessor 217 which communicates control signals to the various valves of the apparatus to initiate and terminate fluid flow within the conduits. Microprocessor 217 may also provided control signals to the various processing stations of the apparatus to initiate specific processing steps.

The programming of the microprocessor may be easily accomplished by one skilled in the art. In another embodiment it may be desirable to pre-program the processing stations to fully automate the use of the present apparatus.

Those skilled in the art may find other variations in the apparatus or other embodiments for the apparatus which are within the scope of the invention described herein.

Having described the invention, what is claimed is:

1. Apparatus for the recovery of cell product contained within capsules in admixture with gellable material and cells, said capsules being disposed in a medium, said apparatus comprising a plurality of stations including:
   (a) a first vessel for holding said capsules and medium, said vessel having at least one intake port for introducing material to the vessel, at least one output port for draining liquids from said vessel, and means for precluding passage of said capsules from said veseel while permitting passage of liquids;
   (b) a source of wash solution in selective fluid communication with said first vessel;
   (c) means for mechanically disrupting the capsule membranes without substantially disrupting the cell membranes, in fluid communication with the output port of said first vessel, to produce a homogenate comprising a solid phase of capsule debris and cells and a liquid phase comprising dissolved cell product, said means including a homogenate output port for the discharge of homogenate;
   (d) a selectively operable source of gelling reagent, disposed upstream of and in fluid communication with said means for disrupting, for mixing said gelling reagent with said gellable material;
   (e) means for separating the solid and liquid components of said homogenate solution, said separating means being in fluid communication with the homogenate output port of said means for disrupting, to yield a liquid cell product-rich solution substantially free of cells, gellable material, and capsule debris.

2. Apparatus of claim 1 further including a second veseel in fluid communication with said separating means for storing said liquid cell product.

3. Apparatus of claim 2 further including a first waste receptacle in fluid communication with the output port of said first vessel for receiving liquid waste.

4. Apparatus of claim 3 further including a second waste receptacle in communication with said separating means for receiving solid waste.

5. Apparatus of claim 2 wherein said first and second vessels includes means for controlling the temperature and pressure of a liquid contained within said vessels.

6. Apparatus of claim 1 wherein said conduits have valve means to selectively regulate the fluid flow within said conduits.

7. Apparatus of claim 6 further comprising pumping means to actively transport fluid between said stations.

8. Apparatus of claim 6 further including a first filtering apparatus disposed downstream of said wash source in the conduit connecting said wash source with said first vessel.

9. Apparatus of claim 8 wherein said filtering apparatus comprises twin serial filter elements of decreasing mesh size.

10. Apparatus of claim 9 wherein said twin filter elements have mesh sizes ranging from 0.45 to 0.2 microns.

11. Apparatus of claim 6 further including a second filtering apparatus disposed downstream of said separating means within the conduit connecting said separating means and said second vessel.

12. Apparatus of claim 11 wherein said filtering apparatus comprises four serial filter elements of decreasing mesh size.

13. Apparatus of claim 12 wherein said filter elements have mesh sizes ranging from 0.6 to 0.1 microns.

14. Apparatus of claim 7 further including a microprocessor in electrical communication with said valves, pumps and stations for automating the operation of said apparatus.

15. Apparatus of claim 1 wherein said cell product is a protein.

16. Apparatus of claim 15 wherein said protein is a monoclonal antibody.

17. Apparatus of claim 1 wherein the elements of said apparatus are closed to form a sterile environment.

* * * * *